United States Patent [19]

Kosmos

[11] Patent Number: 4,645,455
[45] Date of Patent: Feb. 24, 1987

[54] UNIFORMLY FLUORESCING PORCELAIN DENTAL RESTORATIONS

[75] Inventor: Peter Kosmos, Alsip, Ill.

[73] Assignee: Austenal International, Inc., Chicago, Ill.

[21] Appl. No.: 524,721

[22] Filed: Aug. 19, 1983

[51] Int. Cl.$^4$ .............................................. A61C 13/08
[52] U.S. Cl. ................................ 433/203.1; 433/212.1
[58] Field of Search ...................... 433/203, 212, 202; 264/19, 20

[56] References Cited

U.S. PATENT DOCUMENTS 2,301,174  11/1942  Dietz ..................................... 264/19
3,449,832  5/1969   Connan ................................ 433/203
4,167,417  9/1979   Franz et al. ........................... 106/35

Primary Examiner—John J. Wilson

[57] ABSTRACT

A porcelain veneered dental restoration in which UV fluorescing agent is present in each of the opaque, body and incisal layers at a level to provide the restoration with a uniform fluorescence matching that of natural teeth.

2 Claims, 1 Drawing Figure

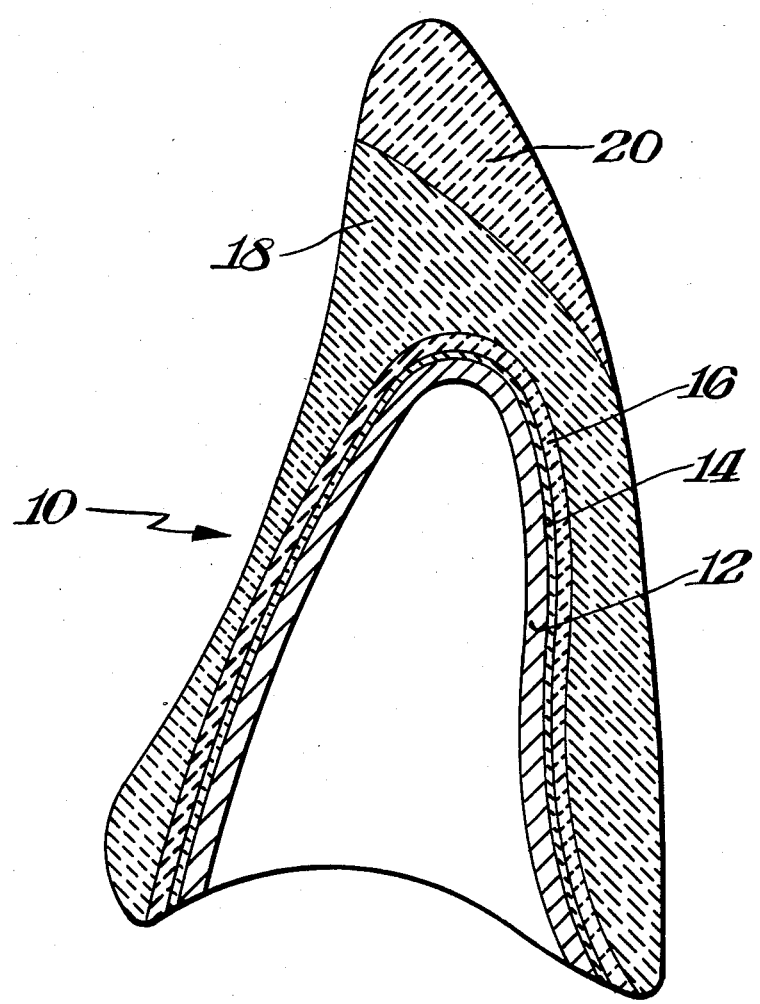

UNIFORMLY FLUORESCING PORCELAIN DENTAL RESTORATIONS

BACKGROUND OF THE INVENTION

This invention concerns the fabrication of a porcelain dental restoration in a manner which provides the restoration with a UV fluorescence matching that of natural teeth.

The appearance of natural teeth varies with the light source to which the teeth are exposed, showing a fluorescence in the yellow-white to blue-white region of the visible spectrum upon exposure to UV light. It is therefore desirable in the fabrication of porcelain dental restorations such as crowns and bridges to simulate not only the color shade but also the fluorescence characteristics of the remaining natural teeth of a patient.

Past attempts at fabricating dental porcelains with desirable fluorescing characteristics under UV light include the addition of uranium oxide compounds, rare earth elements or complex rare earth elements to the porcelain. The use of uranium oxide compounds is not preferred since the compounds are radioactive and their addition results in a yellowish to yellowish-green fluorescence under UV light, which does not adequately simulate the appearance of natural teeth. Addition of rare earth elements or their complexes produces a suitable white fluorescence; the exact color of this white fluorescence depends upon the rare earth elements present, while its intensity is related to the amounts of both the agent and the color pigment present in the porcelain.

A suitable complex rare earth compound for such purpose is disclosed in U.S. Pat. No. 4,167,417. While this pigment produces the desired UV fluorescence in porcelain dental restorations, a uniform intensity of the fluorescence throughout the restoration has yet to be achieved.

It is therefore a primary objective of the present invention to provide a dental restoration having a UV fluorescence simulating that of natural teeth with a uniform appearance throughout the restoration.

SUMMARY OF THE INVENTION

It has now been found that by the controlled addition of a suitable fluorescing agent to each of the opaque, body and incisal layers of a dental restoration, a uniform UV fluorescence in the restoration which simulates that of the natural teeth the restoration replaces can be achieved.

Accordingly, the present invention entails a porcelain veneered dental restoration having an opaque layer, a body layer and an incisal layer, each of the layers containing an effective amount of a UV fluorescing agent.

Preferably, the restoration contains as the fluorescing agent an inorganic pigment of the formula

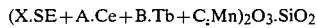

wherein SE is at least one of the elements yttrium, gadolinium and lanthanum; Ce is cerium; Tb is terbium; Mn is manganese; A is 0.005 to 0.1 mole fraction; B is 0.005 to 0.1 mole fraction; C is 0.001 to 0.025 mole fraction; and X is $1.0-(A+B+C)$. Such pigment is preferably employed at a level of from about 1.5 to 10 weight percent in the opaque layer, from about 0.05 to 0.5 weight percent in the body layer and from about 0.02 to 0.2 weight percent in the incisal layer.

Especially suitable is a restoration in which the inorganic pigment is of the approximate composition

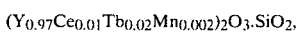

the pigment being present at a level of from about 1.5 to 6 weight percent in the opaque layer, from about 0.1 to 0.2 weight percent in the body layer and from about 0.05 to 0.15 weight percent in the incisal layer.

The present invention also entails a method of fabricating a dental restoration containing an opaque porcelain layer, a body porcelain layer and an incisal porcelain layer to match the level of UV fluorescence of a natural tooth being replaced, which comprises the steps of (a) selecting a color shade which most closely matches the shade of the natural tooth; (b) establishing the level of fluorescence in the natural tooth corresponding to the selected shade of the natural tooth; and (c) incorporating coloring and UV fluorescing agent into each of the opaque, body and incisal layers of the dental restoration in sufficient amount to correspond to the selected color shade and the fluorescence level of the natural tooth.

Further, the present invention comprises an array of unfired dental porcelain formulations of varying color shade for use in the fabrication of veneered dental restorations which comprises opaque, body and incisal formulations approximating the range of color shades found in natural teeth, each of the formulations containing UV fluorescing agent in an amount to approximate the level of fluorescence associated with the natural tooth color shade.

BRIEF DESCRIPTION OF THE DRAWING

The accompanying FIGURE is a schematic cross-sectional view of a typical porcelain veneer crown showing the various layers of the composite structure.

DETAILED DESCRIPTION OF THE INVENTION

The preparation of a porcelain veneered restoration such as the crown 10 of the accompanying FIGURE generally includes the following steps.

A substructure or substrate 12, typically a cast metal framework or a ceramic core or a platinum foil matrix with or without tin plating, is fabricated to receive the porcelain veneer. The substrate 12 may be preconditioned prior to receiving the veneer by such as an oxidation treatment and/or the application of a bonding layer 14 and/or sandblasting. An aqueous slurry of an opaque porcelain powder mixture is then applied and fired to the substrate 12 to form opaque layer 16; the function of opaque layer 16, which becomes chemically bonded to substrate 12, is to mask the appearance of substrate 12 and to provide a colored surface consistent with the final shade of the crown 10. Similarly, a body layer 18 and an incisal layer 20 are formed from body and incisal porcelain powder mixtures to build up the bulk of the tooth anatomy and provide a natural appearance to the restoration 10 resembling the tooth that is being replaced.

These porcelain powder mixtures for such dental fabrication are normally supplied to the dental laboratory in an array of color shades corresponding to recognized color shade guide systems, the shades varying in both color (pigment concentration) and translucence.

The two major shade systems recognized in the United States, for example, are Vita-Lumin and Trubyte Bioform, registered trademarks of Zahnfabrik AG and Dentsply International, respectively, representing some 40 shades. An array of color shades is provided for each of the opaque, body and incisal layers.

A given unfired porcelain powder mixture will therefore usually comprise a blend of base porcelain powder and stained porcelain powder. The base porcelain may be, for example, MicroBond Body Porcelain, MicroBond being a registered trademark of Howmedica, Inc., Dental Division, Chicago, Ill. This porcelain has the following approximate composition in percentage by weight: 68.64 $SiO_2$, 13.76 $Al_2O_3$, 0.36 CaO, 13.46 $K_2O$, 2.29 $Na_2O$ and 1.49 $Li_2O$. The stained porcelain powder is normally a blend of such a base porcelain fritted with various inorganic pigments and then ground to make individual concentrated stained powders. The pigments may be such as zirconium silicate, molybdic trioxide, cobalt aluminate and iron oxide to develop the desired color. The pigments are usually about 20 weight percent of opaque stained porcelain mixtures and about 10 weight percent of body and incisal stained porcelain mixtures. Opacifying agents such as zirconium oxide and tin oxide are also fritted with the base porcelain and then ground and used to develop the desired degree of opacity or translucence.

Since natural human teeth when exposed to UV light fluoresce in the yellow-white to blue-white region of the visible spectrum, a dental restoration of a natural tooth should ideally include a UV fluorescing agent which reflects this characteristic. Although the degree of fluorescence of natural teeth changes with the age of the patient, it has been found to be directly related to the color shade of the tooth. Thus, by establishing this relationship between color shade and fluorescence and by determining the amount of a given fluorescing agent required to impart the desired fluorescence to a given color shade for each of the opaque, body and incisal layers, knowledge of the desired color shade for a restoration sets the agent's level for each of the layers. The precise level for a given agent in a given color shade formulation for a given layer may be established with the aid of UV photography.

Suitable agents for developing fluorescence in dental restorations include, for example, the complex rare earth pigments of the general formula $$(X.SE + A.Ce + B.Tb + C.Mn)_2O_3.SiO_2$$

wherein SE is at least one of the elements yttrium, gadolinium and lanthanum, Ce is cerium, Tb is terbium, Mn is manganese, A is 0.005 to 0.1 mole fraction, B is 0.005 to 0.1 mole fraction, C is 0.001 to 0.025 mole fraction, and X is $1.0-(A+B+C)$.

Such pigments, their preparations and properties are disclosed, for example, in U.S. Pat. No. 4,167,417, which is incorporated herein by reference. Such pigments are preferably present at levels of from about 1.5 to 10 weight percent in formulations for the opaque layer of a restoration, from about 0.05 to 0.5 weight percent in formulations for the body layer and from about 0.02 to 0.2 weight percent in formulations for the incisal layer to provide the desired uniform fluorescence in restorations.

An especially preferred pigment of this class is available as Lumilux Yellow White Z supplied by Riedel-de-Haen Aktiengesellschaft, Hamburg, Federal Republic of Germany. This pigment, of the approximate formula $$(Y_{0.97}Ce_{0.01}Tb_{0.02}Mn_{0.002})_2O_3.SiO_2,$$

is generally incorporated at a level of from about 1.5 to 6 weight percent in the opaque layer formulations, from about 0.1 to 0.2 weight percent in the body layer formulations and from about 0.05 to 0.10 weight percent in the incisal layer formulations. Other rare earth compounds such as those of cerium as well as similar fluorescing agents may of course be included with this pigment to enhance and/or modify the color of the fluorescence of the fired porcelain.

Thus, in fabricating a porcelain dental restoration such as a crown or bridge to match the natural teeth of a patient, the color shade from a standard color shade guide system is selected which most closely matches the color shade of the natural teeth. Then the opaque, body and incisal formulations for this color shade, each of which contains sufficient fluorescing agent to impart the desired fluorescence to the restoration as determined above, are selected and the restoration is prepared by conventional techniques. By incorporating the agent at the determined level in each of the opaque, body and incisal layers, a uniformly fluorescing restoration is obtained.

The following examples are illustrative of the present invention, the scope of which is defined by the appended claims.

EXAMPLE 1

A procelain crown dental restoration for the second upper left bicuspid of a dental patient is prepared by standard dental laboratory procedures employing a cast metal alloy substrate with opaque, body and incisal porcelain veneers. Vita B1[(1)] is selected as the color shade for the restoration since it most closely matches the color shade of the patient's natural teeth. The unfired opaque, body and incisal porcelain mixtures corresponding to this color shade have the following combinations of base porcelain, stained porcelain and fluorescing agent in percentage by weight:

|  | Unfired Porcelain Mixture | | |
| --- | --- | --- | --- |
|  | Opaque | Body | Incisal |
| Base porcelain[(2)] | 91.93 | 95.70 | 99.93 |
| Stained porcelain[(3)] | 6.07 | 4.19 | 0.00 |
| Fluorescing agent[(4)] | 2.00 | 0.11 | 0.07 |

[(1)]Zahnfabrik AG, Bad Sackingen, Federal Republic of Germany
[(2)]MicroBond Body Porcelain, Howmedica Inc., Dental Division, Chicago, Illinois
[(3)]ground fritted mixture of color pigment, opacifying agent and base porcelain containing 20 wt % color pigment in opaque porcelain mixture and 10 wt % color pigment in body and incisal porcelain mixtures
[(4)]Lumilux Yellow White Z, Riedel-de-Haen Aktiengesellschaft, Hamburg, Federal Republic of Germany The color of the restoration when placed in the patient's mouth blends with that of the remaining natural teeth under both natural and UV light, showing a uniform UV fluorescence.

EXAMPLES 2–5

Following the general procedure of Example 1, the following restorations are prepared to match the following color shades:

|  | Example | | | |
|---|---|---|---|---|
| | 2 | 3 | 4 | 5 |
| Color shade | Vita A1 | Vita D2 | Vita A3.5 | Trubyte Bioform 82[1] |
| Opaque layer | | | | |
| Base porcelain | 96.12 | 77.69 | 74.18 | 51.34 |
| Stained porcelain | 2.38 | 19.81 | 22.82 | 44.99 |
| Fluorescing agent | 1.50 | 2.50 | 3.00 | 3.67 |
| Body layer | | | | |
| Base porcelain | 93.96 | 94.61 | 89.94 | 89.49 |
| Stained porcelain | 5.91 | 5.26 | 9.91 | 10.35 |
| Fluorescing agent | 0.13 | 0.13 | 0.15 | 0.16 |
| Incisal layer | | | | |
| Base porcelain | 99.93 | 98.852 | 97.918 | 97.303 |
| Stained porcelain | 0.00 | 1.052 | 1.982 | 2.587 |
| Fluorescing agent | 0.07 | 0.096 | 0.100 | 0.110 |

[1] Dentsply International, York, Pennsylvania

The restorations display a uniform UV fluorescence matching that of the natural teeth they replace.

I claim:

1. A porcelain veneered dental restoration having a substructure and an overlaying opaque layer, a body layer and an incisal layer, each of said layers containing an effective amount of a UV fluorescing agent, wherein said UV fluorescing agent is an inorganic pigment of the formula $$(X.SE + A.Ce + B.Tb + C.Mn)_2O_3 \cdot SiO_2$$

wherein
- SE = at least one of the elements yttrium, gadolinium and lanthanum,
- Ce = cerium,
- Tb = terbium,
- Mn = manganese,
- A = 0.005 to 0.1 mole fraction,
- B = 0.005 to 0.1 mole fraction,
- C = 0.001 to 0.025 mole fraction, and
- X = 1.0 − (A + B + C), and wherein said inorganic pigment is present at a level of from about 1.5 to 10 weight percent in the opaque layer, from about 0.05 to 0.5 weight percent in the body layer and from about 0.02 to 0.2 weight percent in the incisal layer.

2. A porcelain veneered dental restoration having a substructure and an overlaying opaque layer, a body layer and an incisal layer, each of said layers containing an effective amount of a UV fluorescing agent, wherein said UV fluorescing agent is an inorganic pigment of the approximate composition $$(Y_{0.97}Ce_{0.01}Tb_{0.02}Mn_{0.002})_2O_3 \cdot SiO_2,$$

wherein
- Y = yttrium,
- Ce = cerium,
- Tb = terbium, and
- Mn = manganese, and wherein said inorganic pigment is present at a level of from about 1.5 to 6 weight percent in the opaque layer, from about 0.1 to 0.2 weight percent in the body layer and from about 0.05 to 0.10 weight percent in the incisal layer.

* * * * *